(12) United States Patent
Kim et al.

(10) Patent No.: US 7,491,415 B2
(45) Date of Patent: Feb. 17, 2009

(54) **FUNGICIDES COMPOSITIONS COMPRISING THE EXTRACT OF *CHLORANTHUS HENRYI* AND A NOVEL SESQUITERPENE COMPOUND ISOLATED FROM THEM**

(75) Inventors: Sung Uk Kim, Daejeon (KR); Yun Mi Lee, Gyeonggi-do (KR); Ki Duk Park, Daejeon (KR); Tae Hoon Kang, Daejeon (KR); Sung Eun Kim, Daejeon (KR); Mun-Chual Rho, Daejeon (KR); Jae Sun Moon, Daejeon (KR); Won Shik Choi, Daegu (KR)

(73) Assignee: Korea Research Institute of Bioscience and Biotechnology, Yuseong-gu, Daejeon (KR)

( * ) Notice: Subject to any disclaimer, the term of this patent is extended or adjusted under 35 U.S.C. 154(b) by 0 days.

(21) Appl. No.: 11/598,078

(22) Filed: Nov. 13, 2006

(65) Prior Publication Data
US 2007/0154574 A1    Jul. 5, 2007

(30) Foreign Application Priority Data
Dec. 8, 2005    (KR) ............... 10-2005-0119161

(51) Int. Cl.
*A61K 36/00*    (2006.01)
(52) U.S. Cl. ................ 424/773; 424/778; 424/779
(58) Field of Classification Search ............ None
See application file for complete search history.

(56) References Cited
FOREIGN PATENT DOCUMENTS
CN            1364640 A  *  8/2002

OTHER PUBLICATIONS

Kawabata et al., Dimeric Sesquiterpenoid Esters from *Chloranthus serratus*, 1992, Phytochemistry, vol. 31, pp. 1293-1296.*
Tripathi, Pramila et al., "Exploitation of natural products as an alternative strategy to control postharvest fungal rotting of fruit and vegetables," Postharvest Biology and Technology 32, pp. 235-245 (2004).
Dixit, S.N. et al., "Development of a Botanical Fungicide against Blue Mould of Mandarins," J. stored Prod. Res. vol. 31 No. 2, pp. 165-172 (1995).
Ragsdale, N.N. et al., "Social and Political Implications of Managing Plant with Decreased Availability of Fungicides in the United States," Annu. Rev. Phytopathol, 32:545-57 (1994).
Wilson, Charles L. et al., "Biological Control of Postharvest Diseases of Fruits and Vegetables: An Emerging Technology," Annu. Rev. Phytopathol, 27:425-41 (1989).
Reimann, Sven et al., "Fungizide: Risiken Der Resistenzentwicklung Und Suche Nach Neuen Targets," Arch. Phytopath. Plant Prot., 33:329-349 (2000).
Li, Chang-jun et al., "Studies on the Chemical Constituents from the Roots of *Chloranthus henryi*," Yao Xue Xue Bao, 40:525-528 (2005).
Constantine John Alexopoulos, "Introductory Mycology" Second Edition, pp. 134, 135 and 154-163.

* cited by examiner

*Primary Examiner*—Susan Hoffman
*Assistant Examiner*—Catheryne Chen
(74) *Attorney, Agent, or Firm*—The Nath Law Group; William E. Beaumont

(57) ABSTRACT

A fungicidal composition for agricultural use, containing *Chloranthus henryi* extract or a sesquiterpene compound separated from *Chloranthus henryi* extract as an active ingredient, the composition having a antifungal activity against phytopathogenic fungi.

24 Claims, 4 Drawing Sheets

FUNGICIDES COMPOSITIONS COMPRISING THE EXTRACT OF *CHLORANTHUS HENRYI* AND A NOVEL SESQUITERPENE COMPOUND ISOLATED FROM THEM

CROSS REFERENCE TO RELATED CASES

This application claims priority from Korean Patent Application No. 10-2005-0119161, filed Dec. 8, 2005, with the Korean Intellectual Property Office, the entire disclosure of which is incorporated herein by reference.

BACKGROUND OF THE INVENTION

1. Field of the Invention

The present invention relates to a fungicidal composition for agricultural use, which comprises *Chloranthus henryi* extract or a sesquiterpene compound separated from *Chloranthus henryi* extract as an active ingredient, and, in particular, it relates to an eco-friendly fungicidal composition supported by the findings that *Chloranthus henryi* extract or a sesquiterpene compound obtained therefrom exhibit potent antifungal activities against phytopathogenic fungi.

2. Description of the Background

Researches on the development of fungicides for agricultural use against phytopathogenic fungi have been focused on chemically-synthesized fungicides for the past decades. Tripathi, et al., Postharvest Biol. Tec., 32, 235-245, 2004; Dixit, S. N., et al., J. Stored. Prod. Res., 31, 165-172, 1995. However, synthetic fungicides are limited in use because of their potent hazard to ecosystem, including humans and animals, despite superior fungicidal efficacy. Ragsdale, N. N., et al., Annu. Rev. Phytopathol., 32, 545-557, 1994; Wilson, C. L., et al., Annu. Rev. Phytopathol, 27, 425-441, 1989. Further, repeated use of excess commercial fungicides has been shown to cause an increase in resistance of phytopathogenic fungi, thus requiring the development of stable and eco-friendly fungicides. Reimann, S., et al., Arch. Phytopathol. Plant Prot., 33, 329-349, 2000. In particular, considering that plants have less side effects than chemically synthesized fungicides, a need has existed to develop eco-friendly biological fungicides prepared by using unprotected natural plant extracts and plant-derived materials.

To meet these needs, the present inventors investigated plant-derived compounds with inhibitory activity against phytopathogenic fungi in order to develop fungicides for agricultural use from natural resources. Thereby, it was found that *Chloranthus henryi* extract has an inhibitory activity against various human pathogenic and phytopathogenic fungi. *Chloranthus henryi* is a perennial herb growing naturally in China, which falls in *Chloranthaceae* Li C J, et al., Yao Xue Xue Bao, 40, 525-528, 2005. The biological activity about this plant has not been reported.

Thus, the present inventors investigated the antifungal activity of *Chloranthus henryi* extract and compounds obtained therefrom on laboratory scale, and further explored the usefulness against various phytopathogenic fungi causing rice blast(*Magnaporthe grisea*), rice sheath blight(*Corticium sasaki*), tomato gray mold(*Botrytis cinerea*), tomato late blight(*Phytophthora infestans*), wheat leaf rust(*Puccinia recondita*) and barley powdery mildew(*Blumeria graminis* f sp. *hordei*) by using plants grown in the greenhouse. The present invention has been completed by the findings that *Chloranthus henryi* extract and compounds obtained therefrom have potent antifungal activities against phytopathogenic fungi.

Therefore, the present invention provides a fungicidal composition for agricultural use, which contains *Chloranthus henryi* extract and a sesquiterpene compound obtained therefrom having antifungal activity against phytopathogenic fungi.

SUMMARY OF THE INVENTION

The present invention relates to a fungicidal composition for agricultural use, which contains *Chloranthus henryi* extract as an active ingredient and which has antifungal activities against phytopathogenic fungi.

The present invention also relates to a compound of formula (1) separated from the extract and a fungicidal composition for agricultural use containing the compound as an active ingredient.

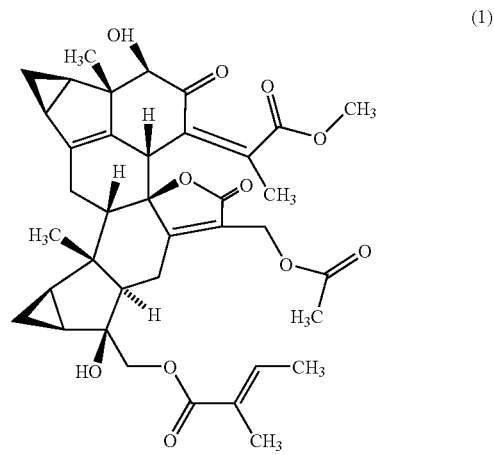

(1)

DETAILED DESCRIPTION OF THE PREFERRED EMBODIMENTS

Figure 1:
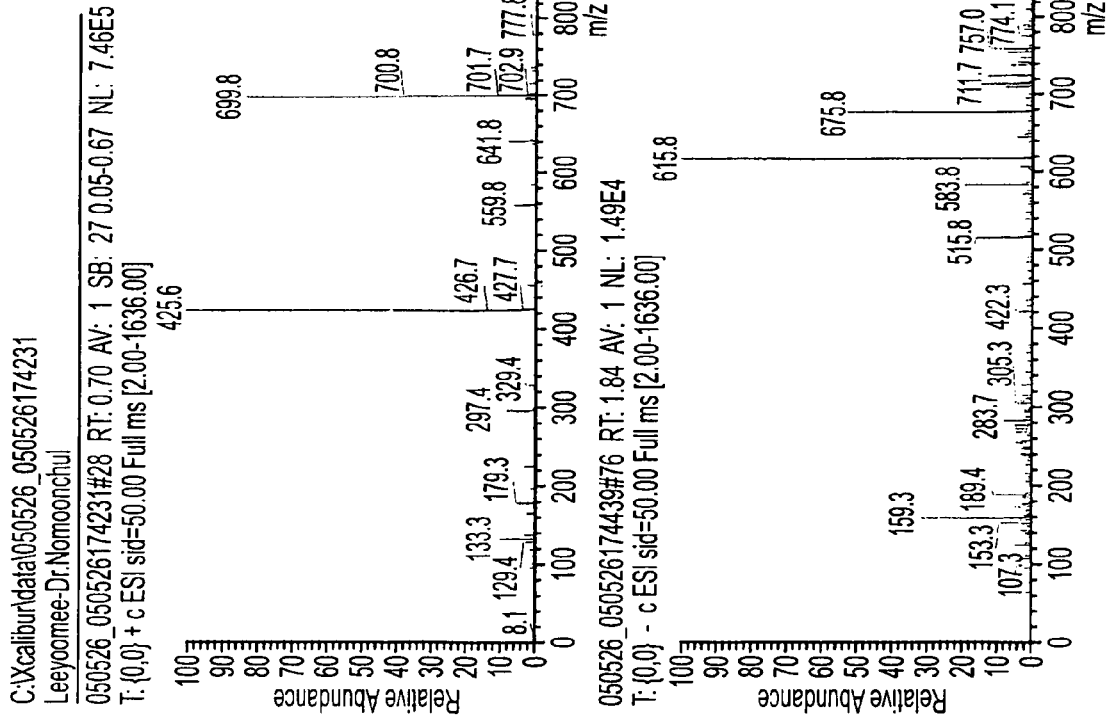
FIG. 1 is a molecular weight analysis spectrum of a compound of formula (1).

The present invention relates to an eco-friendly fungicidal composition for agricultural use, which is supported by the findings that *Chloranthus henryi* extract or a sesquiterpene compound obtained therefrom has potent antifungal activities against phytopathogenic fungi.

In the present invention, the antifungal activities of a sesquiterpene compound separated from *Chloranthus henryi* extract were investigated against various phytopathogenic fungi causing rice blast(*Magnaporthe grisea*), rice sheath blight(*Corticium sasaki*), tomato gray mold(*Botrytis cinerea*), tomato late blight(*Phytophthora infestans*), wheat leaf rust(*Puccinia recondita*) and barley powdery mildew (*Blumeria graminis* f. sp. *hordei*). As a result, it was ascertained that the extract and the compound described herein show potent activities against phytopathogenic fungi causing tomato late blight and wheat leaf rust, and which serve as a basis for a fungicidal composition for agricultural use.

In the present invention, *Chloranthus henryi* extract may be prepared according to the conventional methods, which include any method for extracting from hydrophilic to lipophilic components. That is, any method that can prepare *Chloranthus henryi* extract may be used. Examples of a method for preparing *Chloranthus henryi* extract herein include without limitation distilled water bath extraction method and organic solvent extraction method. Examples of the organic solvent include any organic solvents and various mixtures of water and any organic solvents.

Further, examples of a method for preparing a sesquiterpene compound of formula (1) from *Chloranthus henryi* include without limitation a process entailing:

(a) obtaining methanol crude extract by extracting stem or root of *Chloranthus henryi* with methanol;

(b) obtaining an organic layer by extracting the methanol crude extract with a solvent selected from the group consisting of aliphatic alcohol, aliphatic alcohol aqueous solution, hexane, chloroform and ethyl acetate;

(c) obtaining active fractions with antifungal activities (hexane: chloroform=6:4-chloroform:ethyl acetate=6:4) by performing vacuum evaporation of the organic phase, dissolving with distilled water, extracting with ethyl acetate, adsorbing the organic layer in a normal phase silica chromatography column, and eluting stepwisely while changing the ratios of hexane and chloroform (8:2-2:8) and chloroform and ethyl acetate (8:2-2:8);

(d) obtaining active fraction by adsorbing bioactive fractions in a normal phase silica chromatography column and eluting with hexane and ethyl acetate (5:5);

(e) purifying the active fractions by performing a gel filtration chromatography (Sephadex LH-20) with 100% methanol; and (f) obtaining a compound of formula (1) by HPLC purification and recrystallization.

First, liquid extract is obtained by extracting dried *Chloranthus henryi* followed by filtration. The extracting solvent can be any organic solvents and various mixtures of water and organic solvents. Examples of the aliphatic alcohol include methanol, ethanol, propanol and butanol, and preferably methanol. The extract is concentrated in vacuo, dissolved in distilled water, and extracted with ethyl acetate solvent. Ethyl acetate layer, which is ascertained to have antifungal activity against phytopathogenic fungi, is separated by performing multi-step column chromatography (silica gel and Sephadex LH-20). Compounds with high antifungal activities are purified by HPLC and recrystallized as a single compound.

Thus obtained compound is analyzed with $^1$H-NMR, $^{13}$C-NMR and ESI-MS. In the present invention, a white crystalline compound was obtained, which was characterized as being a sesquiterpene compound of formula 1 ($C_{38}, H_{44}, O_{11}$, MW:676), which showed potent antifungal activities against phytopathogenic fungi.

The fungicidal composition for agricultural use herein contains *Chloranthus henryi* extract or a sesquiterpene compound separated from *Chloranthus henryi* extract as an active ingredient, wherein the active ingredient may be a single component or a mixture thereof depending on the purpose or method of utilization. The mixing ratio may be appropriately determined considering the activity against the target phytopathogenic fungi, for example, by mixing the same amount of each component.

The composition for preparing fungicidal composition herein may contain only active ingredients, or contain a suitable amount of excipients in addition to 0.001-99 wt %, preferably 0.003-30 wt % of the active ingredients. Examples of the excipients include without limitation conventional microorganism formulations, fungicides, antimicrobial activity enhancer, diluents and carriers.

The fungicidal composition for agricultural use herein may be appropriately formulated into for example liquids, emulsions, fumigants, pastes or powders depending on the target plants or application methods. The composition for preparing fungicidal composition herein may be applied to plants according to conventional method, for example, by treatments of coating, immersing, fumigating and spraying, which may also be applied to soil or leaves, seeds, flowers and fruits of target plants in combination of diluents.

Preferably, the fungicidal composition for agricultural use is applied when phytopathogenic fungi proliferates, which depends on the target plants, for example, generally during the periods of sowing, growing and harvesting of plants.

The amount of the fungicidal composition for agricultural use herein may appropriately be determined considering the kinds of plants, pathogenic fungi and application methods, for example, 0.33-2 g of composition or 33-200 μg/plant of active ingredients per agriculture area ($m^2$).

EXAMPLES

The present invention is described more specifically by the following Examples. Examples herein are meant only to illustrate the present invention, but in no way to limit the scope of the claimed invention.

Example 1

Preparation of *Chloranthus henryi* Crude Extract

Stems and roots of *Chloranthus henryi* purchased from Plant Extract Bank of Plant Diversity Research Center in Korea Research Institute of Bioscience and Biotechnology were used in the present invention. 3.9 kg of the dried stems and roots of *Chloranthus henryi* were minced and pulverized, and then added with 15 L of methanol. The mixture was stored at room temperature for 48 hours and filtered. The resulting liquid phase was concentrated in a vacuum evaporator, thereby providing methanol crude extract.

Example 2

Preparation of Organic Solvent Extract From *Chloranthus henryi* Crude Extract 39.3 g out of the 329.5 g of the methanol crude extract prepared in Example 1 was completely dissolved in 500 mL of distilled water, and added with hexane, chloroform and ethyl acetate, followed by fractionation, thereby providing 0.76 g, 0.61 g and 0.49 g of organic phases, respectively. The antifungal activities of the organic solvent layers were examined, and the antifungal activities against various phytopathogenic fungi were ascertained in hexane, chloroform and ethyl acetate layers. Antifungal activities of methanol crude extract and organic solvent extract prepared in Examples 1 and 2 against various phytopathogenic fungi are shown in table 1.

TABLE 1

In vitro antifungal activities of *Chloranthus henryi* extract against various phytopathogenic fungi*

| Phytopathogenic fungi | methanol | hexane | chloroform | ethyl acetate | distilled water |
|---|---|---|---|---|---|
| *Alternaria kikuchiana* | 15 | — | 19 | — | — |
| *Botrytis cinerea* | 23 | — | 25 | — | — |
| *Colletotrichum lagenarium* | 12 | — | 18 | — | — |
| *Fusarium oxysporum* | 11 | — | 15 | — | — |
| *Magnaporthe grisea* | 31 | 18 | 35 | 18 | — |
| *Pythium ultimum* | 27 | 17 | 29 | 16 | — |

*Paper disks (diameter: 8 mm) including solvent extract (0 5 mg) were loaded on potato dextrose agar medium containing each fungus and the plates were incubated for 2-5 days. Diameters of clear zones were measured and indicated in mm.

Example 3

Separation of a Sesquiterpene Compound from *Chloranthus henryi*

Methanol crude extract prepared in Example 1 was dissolved in 1 L of distilled water, and added with 1 L of ethyl acetate, followed by extraction to form an ethyl acetate layer. The ethyl acetate layer containing active ingredients was concentrated in vacuo. The residue was adsorbed on a normal phase silica chromatography column (Merck, Kiesegel 60, 230-400 mesh). Active compounds were fractionated stepwise while changing the ratios of hexane and chloroform (8:2-2:8) and chloroform and ethyl acetate (8:2-2:8), followed by investigation of the antifungal activities of the fractions. Only the fractions with ascertained antifungal activities (i.e. hexane:chloroform=6:4 to chloroform:ethyl acetate=6:4) were collected and concentrated. Partially purified active fraction was obtained by eluting with hexane:ethyl acetate=5:5 in a normal phase silica chromatography column (Merck, Kiesegel 60, 230-400 mesh). This fraction was subjected to gel filtration chromatography (Sephadex LH-20) by using 100% methanol as a solvent, thereby providing a fraction with the highest antifungal activity. A single compound (650.4 mg) was purified from the active fraction via HPLC and recrystallization. The HPLC column used was Watchers ODS-4103 AP (5μ, 4.6×250 mm) column manufactured by Daiso company (Japan).

Example 4

Structure Analysis of the Sesquiterpene Compound

Figure 2:
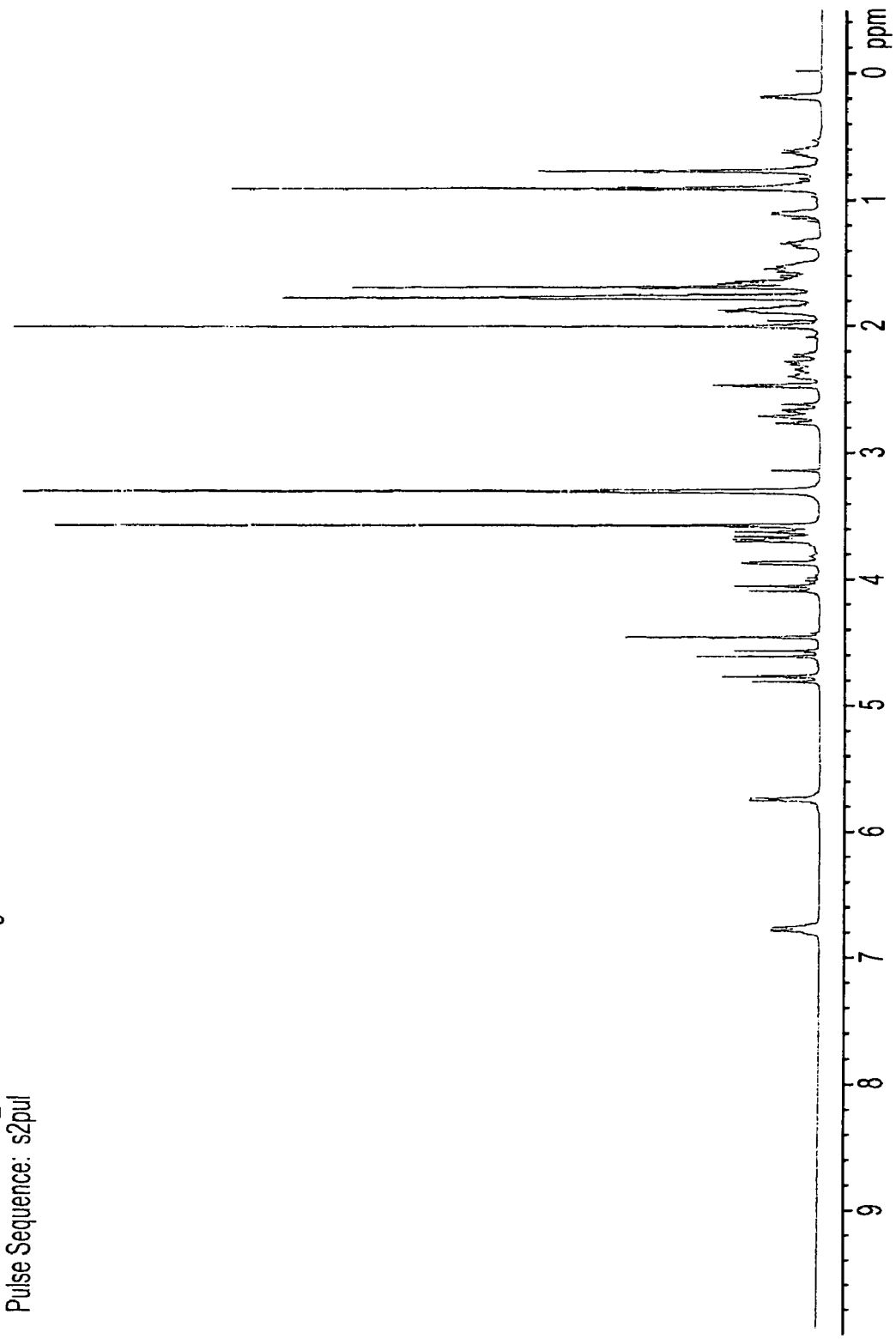
FIG. 2 is a $^1$H NMR spectrum of a compound of formula (1).
Figure 3:
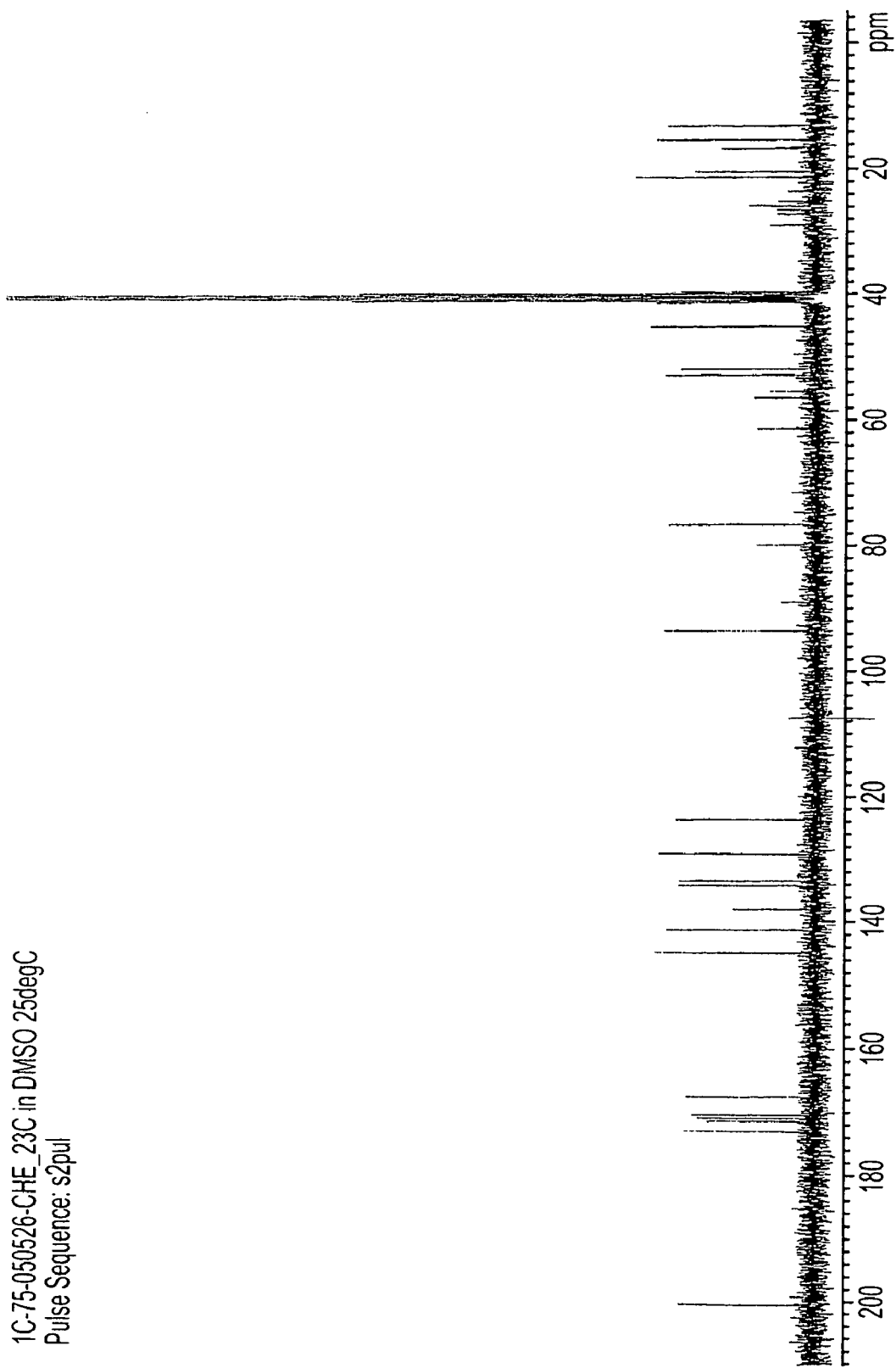
FIG. 3 is a $^{13}$C NMR spectrum of a compound of formula (1).
Figure 4:
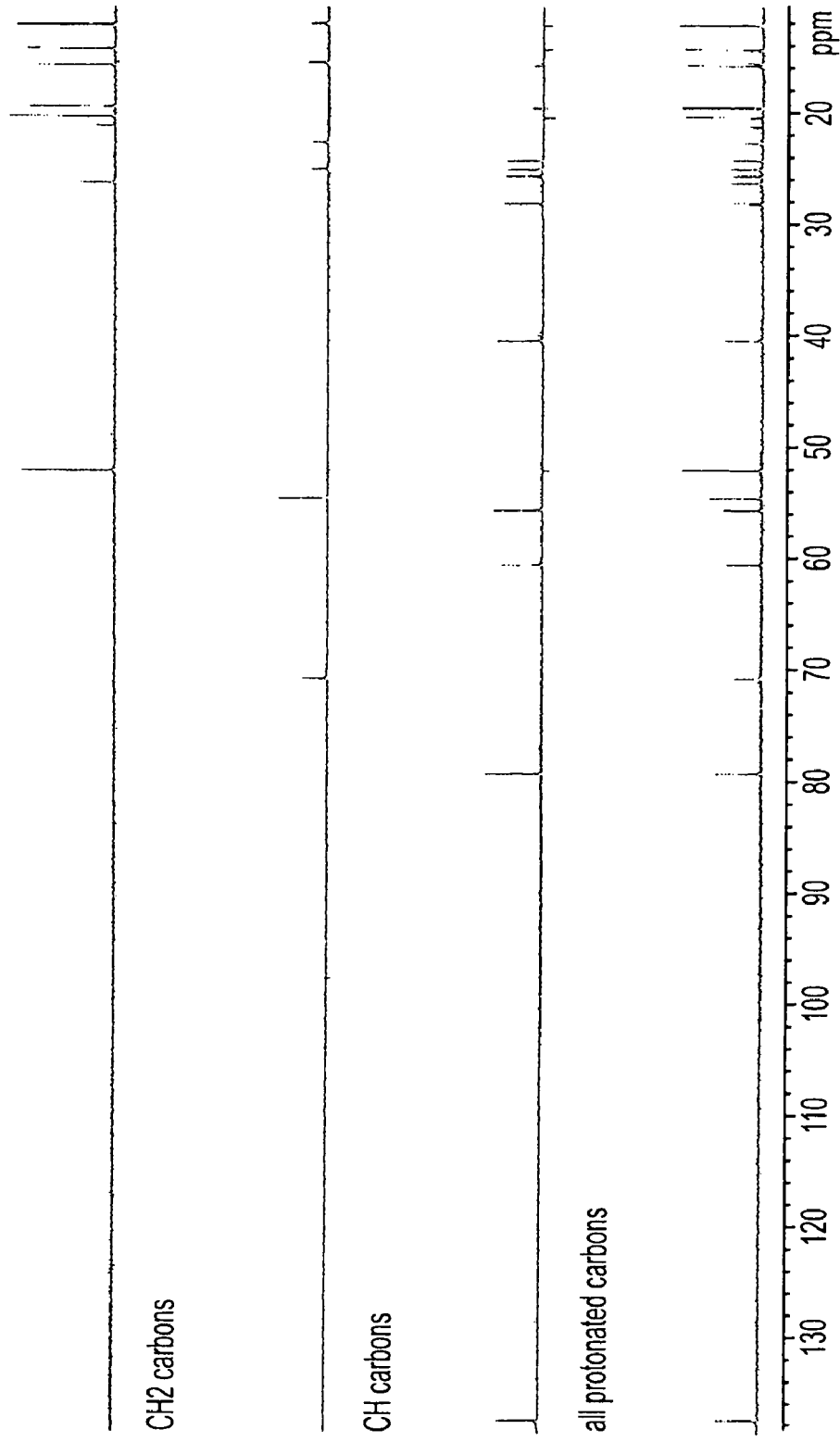
FIG. 4 is a DEPT NMR spectrum of a compound of formula (1).

The structure of the purified compound was analyzed by various NMR (Varian UNITY 300 MHz, 500 MHz NMR) techniques, thereby providing $^1$H, $^{13}$C, COSY, HMQC and HMBC spectra. Further, molecular weight and formula were determined by using mass spectrometry (Hewlett packard 5989A). The results are provided in FIGS. 1-4.

Compound family: Sesquiterpene
Molecular formula: $C_{38}H_{44}O_{11}$,
Molecular weight: m/z 675 [M-H]$^+$, 699 [M+Na]$^+$
Specific rotation: $\{\alpha\}^{25}_D$=−135°(C 0.1, DMSO)

$^1$H-NMR (DMSO-d$_6$): 1.9(ddd), 0.2(ddd), 0.9(ddd), 1.9 (m), 3.9(d), 3.72(s), 1.72(s), 0.93(s), 2.40(br d), 2.75(ddd), 1.55(ddd), 0.65(ddd), 1.13(ddd), 1.37(ddd), 1.62(dd), 2.3(dd), 2.7(dd), 1.68(dd), 4.6(d), 4.8(d), 0.8(s), 3.67(d), 4.10 (d), 6.81(br dd), 1.79(s), 1.80(s)

$^{13}$C-NMR (DMSO-d$_6$): 25.4(CH), 15.4(CH$_2$), 24.1(CH), 140.4(C), 132.4(C), 40.2(CH), 144.0(C), 200.3(C), 79.0(CH), 50.9(C), 133.3(C), 170.3(C), 19.4(CH$_3$), 15.6(CH$_3$), 24.9(CH$_2$), 24.8(CH), 11.9(CH$_2$), 27.9(CH), 75.7 (C), 60.4(CH), 22.5(CH$_2$), 172.5(C), 92.7(C), 55.5(CH), 44.2 (C), 122.7(C), 170.9(C), 54.4(CH$_2$), 26.2(CH$_3$), 70.5(CH$_2$), 167.0(C), 128.1(C), 137.1(CH), 14.2(CH$_3$), 12.0(CH$_3$), 169.9(C), 20.2(CH$_3$)

A sesquiterpene compound of formula (1) purified from *Chloranthus henryi* is white crystalline. The compound had molecular formula of $C_{38}H_{44}O_{11}$ (MW: 676) and was designated CHE-23C. The structure of this compound is shown as formula 1.

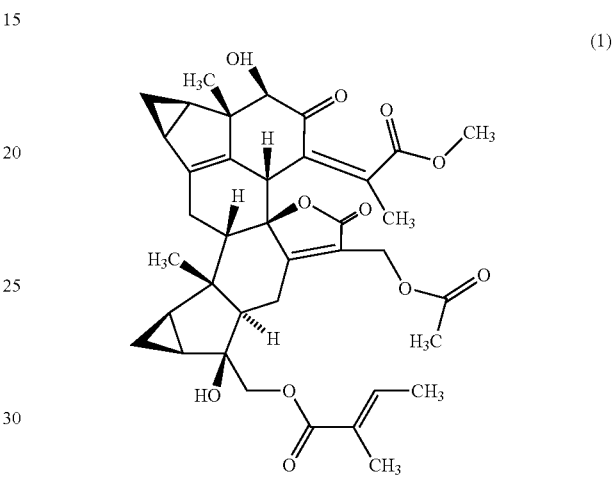

(1)

Example 5

Examination of Antifungal Activities of the Sesquiterpene Compound Against Phytopathogenic Fungi Minimal inhibitory concentration (MIC) was measured to investigate the antifungal activities of the sesquiterpene compound of formula (1) isolated from *Chloranthus henryi* against phytopathogenic fungi. Further, in vivo antifungal activity against phytopathogenic fungi was also investigated by using plants grown in the greenhouse. Names of various plant diseases and phytopathogenic fungi are shown in table 2.

TABLE 2

Plant diseases and phytopathogenic fungi used in in vivo experiments

| Abbr. | Diseases | Phytopathogenic fungi |
|---|---|---|
| RGB | Rice blast | *Magnaporthe grisea* |
| RSB | Rice sheath blight | *Corticium sasaki* |
| TGM | Tomato gray mold | *Botrytis cinerea* |
| TLB | Tomato late blight | *Phytophthora infestans* |
| WLR | Wheat leaf rust | *Puccinia recondita* |
| BPM | Barley powdery mildew | *Blumeria graminis f. sp. hordei* |

Determination of Antifungal Activity (MIC) Against Phytopathogenic Fungi in Agar Medium

*Alternaria kikuchiana, Botrytis cinerea, Colletotrichum lagenarium, Fusarium oxysporum, Magnaporthe grisea, Pythium ultimum, Phytophthora infestans* and *Rhizoctonia*

*solani* were sufficiently grown in potato dextrose agar medium at 25° C. for 7-14 days, and used as an inoculum. *Chloranthus henryi* extract and a sesquiterpene compound obtained therefrom were prepared via 2-fold serial dilutions using sterilized distilled water. This compound was mixed with sterilized potato dextrose agar medium maintained at 50° C. in the ratio of 9:1, and 5 mL of the mixture was poured into each plate to a final concentration of 128-0.5 μg/mL. When the medium was solidified, agar blocks (diameter: 5 mm) cut from the periphery of fungi grown adequately were inoculated on each plate. After cultivation at 25-3020 C. for 1-2 days, MIC was determined as the lowest concentration of the compound that completely inhibited the growth of the fungi by comparing with a control plate not containing the compound.

As shown in table 3, MICs were 4 μg/mL and 1 μg/mL against fungi, a causative agent of rice blast(*Magnaporthe grisea*) and ginseng damping-off(*Pythium ultimum*), respectively, thus showing the presence of potent antifungal activities.

TABLE 3

In vitro antifungal activities of sesquiterpene compound (CHE-23C)

| Test fungi | MIC (μg/mL) |
| --- | --- |
| *Alternaria kikuchiana* | 8 |
| *Botrytis cinerea* | 8 |
| *Colletotrichum lagenarium* | 8 |
| *Fusarium oxysporum* | 16 |
| *Magnaporthe grisea* | 4 |
| *Pythium ultiinum* | 1 |
| *Rhizoctonia solani* | 16 |

(2) Evaluation of in vivo Control Efficacy Against Phytopathogenic Fungi in the Greenhouse To investigate the in vivo protective activities against various phytopathogenic fungi, 2 pots per each plant pathogen were treated with fungi causing rice blast(*Magnaporthe grisea*), rice sheath blight(*Corticiutu sasaki*), tomato gray mold(*Botrytis cinerea*), tomato late blight (*Phytophthora infestans*), wheat leaf rust(*Puccinia recondita*) and barley powdery mildew(*Blumeria graminis* f. sp. *hordei*), respectively. Plants such as rice (*Oryza sativa* L., cv. Nakdong, tomato (*Lycopersicon esculentum* Mill., cv. Seokwang) and wheat (*Triticum aestivum* L., cv. Chokwang) were grown in the greenhouse (25±5° C.) for 1-3 weeks in plastic pots (diameter: 4.5 cm) filled with commercial horticulture nursery medium. The test compound was dissolved in dimethyl sulfoxide, and diluted with distilled water containing 250 μg/mL of Tween 20, where the final concentration of dimethyl sulfoxide was 10%. As a control group, distilled water containing 10% dimethyl sulfoxide and 250 μg/mL of Tween 20 was used. Seedlings were sprayed until run-off with the prepared compound solution. The treated plant seedlings were allowed to dry for 24 hours at room temperature and the plants were inoculated with various phytopathogenic fungi. Infected leaf area was measured with regard to rice blast and wheat leaf rust (after 7 days), rice sheath blight (after 8 days) and tomato gray mold and tomato late blight (after 3 and 4 days, respectively), and control values were obtained by using the mathematical formula in table 4.

Of them, potent control values of the compound were observed against *Phytophthora infestans* and *Puccinia recondita* in the greenhouse experiments as shown 10 in TABLE 4.

TABLE 4

In vivo control values (%)* of sesquiterpene compound (CHE-23C)

| Concentration (ppm) | Diseases* | | | | | |
| --- | --- | --- | --- | --- | --- | --- |
| | RCB | RSB | TGM | TLB | WLR | BPM |
| 100 | 72 | 69 | 36 | 93 | 100 | 17 |
| 33 | 50 | 50 | 14 | 91 | 87 | 0 |
| 11 | 67 | 50 | 7 | 29 | 80 | 0 |

$$\text{Control value}(\%) = \left(1 - \frac{\text{Infected leaf area of treated plants}}{\text{Infected leaf area of untreated plants}}\right) \times 100$$

*RCB: rice blast, RSB: rice sheath blight, TGM: tomato gray mold, TLB: tomato late blight, WLR: wheat leaf rust, BPM: barley powdery mildew Example 6

Acute Toxicity Test of *Chloranthus henryi* Extract and Sesquiterpene Compound

To perform an acute toxicity test of *Chloranthus henryi* extract and the sesquiterpene compound of formula (1), 6-week-old ICR mice (♂, 25 g, Korean Bio Corp.) were divided into 4 groups with two mice per each group, and raised under the condition of 22±3° C., 55±10% (humidity), 12L/12D (intensity of illumination). The mice were adapted for 1 week, and freely fed with foods for test animals (Jeil Feed Corp., Korea, for mouse and rat) and sterilized water.

*Chloranthus henryi* extract and the sesquiterpene compound of formula (1) were dissolved in a small amount of dimethyl sulfoxide (DMSO), and diluted with 1% carboxylmethyl cellulose. Four groups of mice were orally administered with 540 mg/kg, 180 mg/kg, 60 mg/kg and 20 mg/kg, respectively. Control group was administered with 1% carboxylmethyl cellulose. For 7 days after the administration, the presence of side effects or mortality was observed as follows. Specifically, it was observed at intervals of 1, 4, 8 and 12 hours after the administration on the day of administration. The changes in clinical signs and mortality of animals after administration were observed twice everyday for 7 days, i.e., in the morning and in the afternoon.

Further, the internal organs of the dead mice were examined through macroscopic observation after necropsy on the 7th day. The change in body weight of animals by *Chloranthus henryi* extract and sesquiterpene compound of formula (1) was observed everyday after administration.

As a result, no significant gross findings caused by the test materials were observed in all treated groups, and all the mice in the maximum dosage group (540 mg/kg) survived, thus showing that $LD_{50}$ is higher than 540 mg/kg.

As described above, *Chloranthus henryi* extract and the compound of formula (1) separated therefrom show potent antifungal activities against phytopathogenic fungi, and are, thus, applicable for an eco-friendly fungicidal composition for agricultural use.

What is claimed is:

1. A fungicidal composition comprising at least a compound of formula (1) as an active ingredient separated from an extract of *Chloranthus henryi* as an active ingredient:

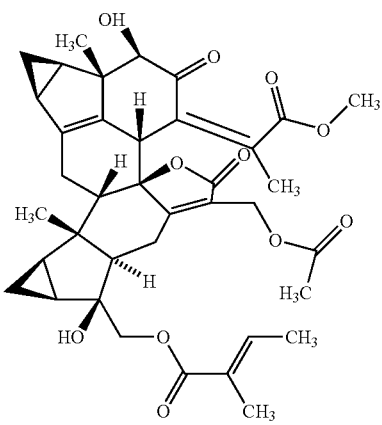

and an excipient.

2. The fungicidal composition of claim 1, wherein the extract of *Chloranthus henryi* is extracted from *Chloranthus henryi* with a solvent comprising an organic solvent, water or a mixture thereof.

3. The fungicidal composition of claim 1, which exhibits antifungal activity against fungi selected from the group consisting of pear leaf spot (*Alternaria kikuchiana*), tomato gray mold (*Botrytis cinerea*), cucumber anthracnose (*Colletotrichum lagenarium*), radish fusarium wilt (*Fusarium oxysporum*), rice blast (*Magnaporthe grisea*), ginseng damping-off (*Pythium ultimum*), tomato late blight (*Phytophthora infestans*), rice sheath blight (*Rhizoctonia solani, Corticium sasaki*) and wheat leaf rust (*Puccinia recondite*).

4. The fungicidal composition of claim 1, wherein the extract of *Chloranthus henryi* is extracted with a lower aliphatic alcohol.

5. The fungicidal composition of claim 4, wherein the lower aliphatic alcohol is methanol.

6. The fungicidal composition of claim 1, further comprising a microorganism formulation, fungicide, or antimicrobial activity enhancer.

7. The fungicidal composition of claim 1, which is in a form of liquid or emulsion.

8. The fungicidal composition of claim 1, which is in a form of a paste or solid.

9. An isolated and purified sesquiterpene compound of formula (1).

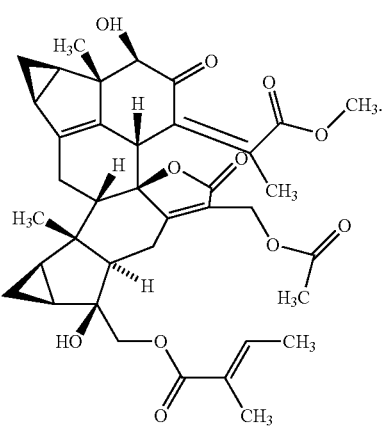

10. A method of separating a compound of formula (1) of claim 9 from *Chloranthus henryi*, the process comprising: (a) obtaining methanol crude extracts by extracting stem or root of *Chloranthus henryi* with methanol; (b) obtaining an organic layer by extracting the methanol crude extracts with a solvent selected from the group consisting of aliphatic alcohol, aliphatic alcohol aqueous solution, hexane, chloroform and ethyl acetate; (c) obtaining fractions with antifungal activity from the organic layer of step (b) by eluting the organic layer by changing a ration of hexane:chloroform stepwise from 8:2 to 2:8, and then chloroform:ethyl acetate from 8:2 to 2:8; (d) obtaining a fraction from step (c) by adsorbing fractions on a phase silica chromatography column and eluting with hexane:ethyl acetate at 5:5 ratio; (e) purifying the fraction step (d) by performing gel filtration chromatography with 100% methanol; and (f) obtaining the compound of formula (1) by HPLC purification and recrystallization.

11. The method of claim 10, wherein step (b), the extract solvent is ethyl acetate.

12. A method of treating soil or plants for fungi, which comprises applying a fungically effective amount of the composition of claim 1, to soil or plants.

13. The method of claim 12, wherein said composition is applied to said soil.

14. The method of claim 12, wherein said composition is applied to said plants.

15. The method of claim 12, wherein said fungi treated is selected from the group consisting of pear leaf spot (*Altemaria kikuchiana*), tomato gray mold (*Botrytis cinerea*), cucumber anthracnose (*Colletotrichum lagenarium*), radish fusarium wilt (*Fusarium oxysporum*), rice blast (*Magnaporthe grisea*), ginseng damping-off (*Pythium ultimum*), tomato late blight (*Phytophthora infestans*), rice sheath blight (*Rhizoctonia solani, Corticium sasaki*) and wheat leaf rust (*Puccinia recondite*).

16. The method of claim 15, wherein said fungi treated is tomato late blight (*Phytophthora infestans*).

17. The method of claim 15, wherein said fungi treated is wheat leaf rust (*Puccinia recondite*).

18. The method of claim 12, wherein the soil or plants are in a greenhouse.

19. The method of claim 10, wherein the extraction solvent of step (b) is an aliphatic alcohol.

20. The method of claim 19, wherein the aliphatic alcohol is selected from the group consisting of methanol, ethanol, propanol and butanol.

21. The method of claim 20, wherein the aliphatic alcohol is methanol.

22. The fungicidal composition of claim 1, which comprises 0.001-99 wt % of the compound of the formula (1).

23. The fungicidal composition of claim 22, which comprises of 0.003-30 wt % of the compound of the formula (1).

24. The fungicidal composition of claim 1, wherein the excipient comprises a mixture of dimethyl sulfoxide and water.

* * * * *